(12) United States Patent
Pereira et al.

(10) Patent No.: US 6,727,209 B2
(45) Date of Patent: Apr. 27, 2004

(54) BIPHASIC COMPOSITION INDUCED BY POLYDEXTROSE AND SUCROSE

(75) Inventors: Daniel Pereira, Stratford, CT (US); Robert D. Sabin, Newtown, CT (US); Rosa Paredes, Shelton, CT (US); May Shana'a, Trumbull, CT (US)

(73) Assignee: Unilever Home & Personal Care, USA, division of Conopco, Inc., Greenwich, CT (US)

( * ) Notice: Subject to any disclaimer, the term of this patent is extended or adjusted under 35 U.S.C. 154(b) by 42 days.

(21) Appl. No.: 10/218,288

(22) Filed: Aug. 14, 2002

(65) Prior Publication Data

US 2004/0038837 A1 Feb. 26, 2004

(51) Int. Cl.⁷ ............................. C11D 1/00; C11D 3/22; C11D 3/37
(52) U.S. Cl. ..................... 510/130; 510/159; 510/405; 510/417; 510/421; 510/426; 510/470; 510/474; 510/475; 510/483; 510/535
(58) Field of Search ................. 510/130, 159, 510/405, 417, 421, 420, 470, 474, 475, 483, 535

(56) References Cited

U.S. PATENT DOCUMENTS

| | | |
|---|---|---|
| 3,718,609 A | 2/1973 | Weimer |
| 3,810,478 A | 5/1974 | Olson, Jr. |
| 6,429,177 B1 * | 8/2002 | Williams et al. ............ 510/130 |

FOREIGN PATENT DOCUMENTS

| EP | 0 116422 B1 | 8/1984 |
|---|---|---|

* cited by examiner

Primary Examiner—Brian P Mruk
(74) Attorney, Agent, or Firm—Ronald A. Koatz

(57) ABSTRACT

The invention relates to use of polydextrose in combination with sucrose to induce biphasic liquid formation. Salt may be optionally used.

10 Claims, No Drawings

BIPHASIC COMPOSITION INDUCED BY POLYDEXTROSE AND SUCROSE

FIELD OF THE INVENTION

The present invention relates to aqueous liquid cleansing compositions which are biphasic in nature. More specifically, such compositions are characterized by having (assuming they have been standing a sufficiently long period of time after shaking) both an upper aqueous layer and a separate lower aqueous layer. In the subject invention, formation of the biphasic liquids is induced by use of sufficient amount of polydextrose in combination with sucrose. In preferred embodiment, the polydextrose is within an approximate molecular weight window. Use of sucrose widens the window of polydextrose which can be used and lowers the levels of polydextrose necessary to achieve biphasic effect.

BACKGROUND

Biphasic liquids defined by the general fact that the liquid is divided into two phases are not new. Most of these liquids comprise both one layer which is an aqueous layer and a second layer comprising a water immiscible oily material.

U.S. Pat. No. 3,718,609 to Weimer, for example, discloses a liquid detergent composition having an aqueous layer and a layer of liquid water immiscible oily material. When shaken, the liquid forms a temporary oil-in-water emulsion.

Similarly, U.S. Pat. No. 3,810,478 to Olson Jr. et al. discloses a two phase shampoo composition made by preparing substantially polar and lipophilic portions of a shampoo composition.

Biphasic compositions comprising an upper and lower aqueous phase are also disclosed in the art. U.S. Ser. No. 09/643,142 to Williams et al., entitled "A Separating MultiPhase Personal Wash Composition in a Transparent or Translucent Package" discloses biphasic compositions comprising:

(a) 5 to 35% surfactant;

(b) 1 to 12% thickener;

(c) 4 to 20% polyalkylene glycol; and (d) sufficient non-chelating mineral salt to induce phase separation.

While the total amount of salt/electrolyte is not specifically discussed in the above specification, it is apparent from the examples that the amount sufficient to induce formation of biphasic layer is at least in the order of 4%, 5%, 6% and greater. By contrast, in the subject invention, salt is not required at all for biphasic formation and, if used, is generally in an amount less than 4%, preferably about 3% by wt. or less and more preferably about 2% by wt. or less. As discussed in the specification below, using small amounts of salt (i.e., about 0.5% to 3%, preferably 0.5% to 1%) does allow less amount of polydextrose to be used to induce biphasic formation.

Unlike the biphasic compositions in the Williams et al. specification, the biphasic compositions of the subject invention are induced by a combination polydextrose and sucrose (and optionally salt). The biphasic compositions of the invention are stable and do not require either thickener or polyalkylene glycol as is required by the compositions of Williams.

EP 0,116,422 to Reckett and Coleman also discloses multi-layered compositions in which two liquids are dispersible and which separate on standing. Again, at least 6% salt/electrolyte (e.g., sodium hexamataphosphate) are required in these compositions (see page 4, lines 17–19). The biphasic liquids of the invention are induced by polydextrose in combination with sucrose, not salt, and no salt is required, although small amounts (e.g., up to about 4%, preferably about 3% or less, more preferably about 1.5% or less, more preferably about 1% or less) may be used. Use of small amounts of salt tend to allow use of less sucrose and/or polydextrose.

In some preferred embodiments of the invention (e.g., where MW of polydextrose is above 1800) use of some salt is preferred to help stability of lower aqueous phase which tends to be more opaque when higher MW polydextrose (e.g., above 1800) are used.

In addition, the compositions of the subject invention are preferably used in translucent or transparent compositions (i.e., for the sensorial benefit) and such is not taught or suggested in EP 0,116,422.

Applicants have filed a co-pending application on same date as subject application in which biphasic as induced by use of polydextrose alone (and optionally salt depending on levels of polydextrose). The subject invention differs from said application in that there is required the use of sucrose in combination with polydextrose and this combination of polydextrose and sucrose provides greater flexibility as to amount of polydextrose used (with or without salt). Further, while the co-pending application requires polydextrose of defined molecular weight, such is not believed required by the present invention (although, as noted above, where MW of polydextrose is above 1800, preferably minimal amounts of salt, e.g., at least 0.1%, preferably at least 0.5%, should be used to help stabilize the lower, more opaque layer formed from the use of higher MW polydextrose; where no salt is used, preferably molecular weight of polydextrose is below 1500 and more preferably below 1200).

BRIEF DESCRIPTION OF INVENTION

Applicants have now found that biphasic liquids (e.g., liquids which separate into top and bottom aqueous liquids) may be induced by addition of sufficient quantity of specifically defined polydextrose in combination with sucrose. This induction can occur with or without use of salt, although use of salt may lower amount of polydextrose used (and is also preferred when MW of polydextrose is above 1800; when such polydextrose is used, use of stabilizer, e.g., xanthan gum, is also preferred). Very low amounts of polydextrose (e.g., as low as about 2.5% by wt.) can be used if sucrose and/or surfactant levels are sufficiently high.

More specifically, the present invention comprises liquid personal cleansing compositions comprising:

(1) 5% to 75%, preferably 6% to 40% by wt. of a surfactant selected from the group consisting of anionic surfactants, nonionic surfactants, amphoteric/zwitterionic surfactants, cationic surfactants and mixtures thereof;

(2) at least about 2.5%, more preferably at least 10% by wt. of polydextrose or mixture of polydextrose molecules. It is preferred, although not required that polydextrose have a degree of polymerization (e.g., number of linking glucose units) of 4 to 22 (this corresponds to MW of about 600 to about 3600);

(3) at least about 2.5% to 50% sucrose; and (4) balance water and minors.

In a second embodiment of the claims, the invention comprises compositions wherein at least 0.5%, preferably at least 1%, more preferably at least 2% salt is used. Generally slightly higher salt allows use of slightly less polydextrose.

In another embodiment of the invention, when polydextrose of MW above 1800 is used, it is also preferred to use some salt. It is further preferred to use some stabilizer (e.g., xanthan gum, carbopol) to stabilize the generally more opaque lower layer.

DETAILED DESCRIPTION OF THE INVENTION

The present invention relates to biphasic liquid cleansing-compositions wherein the formation of the biphasic liquid is induced by the addition of sufficient amount of polydextrose in combination with sucrose. Preferably, the degree of polymerization (defining number of linking glucose groups) of the polydextrose is 4 to 22.

More specifically, the invention comprises:
(1) 5% to 75% by wt. of a surfactant selected from the group consisting of anionic surfactant, nonionic surfactants, amphoteric/zwitterionic, cationic surfactant and mixtures thereof;
(2) at least 2.5%, preferably 10% by wt. polydextrose; preferably, although not necessarily, the degree of polymerization (i.e., number of linking glucose units) of the polydextrose is 4 to 22 corresponding to a MW of 600 to 3600; preferably MW is 700 to 1800, more preferably 900 to 1500 and more preferably 900 to 1200 (at higher MW polydextrose, use of at least 0.1% to, preferably at least 0.5% salt is preferred as is, even more preferred, use of some additional stabilizer);
(3) at least about 2.5% sucrose; and
(4) balance water and minors.

As noted, when polydextrose of MW above 1800 is used, some salt is preferably used.

The general concept behind the invention is that, when sufficient amount of specified polydextrose is added in combination with sucrose, phase separation occurs. The sucrose lower level of polydextrose need to achieve the effect. Different surfactant systems can be used and the specific type of surfactants is not a limiting factor.

The inventive compositions may be used in combination with a transparent package in order to view the liquid. Thus, in one embodiment, the invention also comprises a system comprising said transparent or translucent package in combination with the liquid.

Typically, once the biphasic composition is formed (e.g, the composition "settles" after having been shaken), the viscosity of the lower layer is lower than that of the upper layer.

Also, the density of lower layer is typically greater than that of upper layer.

Typically, in such biphasic liquids, there is no recrystallization visible after composition has been standing for 6 months at room temperature.

In a second embodiment of the invention, a small amount of salt is used and the amount of polydextrose needed to induce biphasic liquid may be reduced. More specifically, in this embodiment, the composition comprises at least 0.5% salt and at least 2.5% polydextrose.

In a third embodiment, the polydextrose is of MW above 1800 and some salt (at least 0.1%, preferably at least 0.5%) is used. More preferably, some stabilizer is added to this embodiment.

The various components of the composition are discussed in greater detail below.

Surfactant

The surfactant generally will comprise 5 to 75% by wt. of the total composition.

The surfactant is a surfactant which may be selected from the group consisting of anionic surfactants, nonionic surfactants, amphoteric/zwitterionic surfactants, cationic surfactants and mixtures thereof. Preferably, there will be at least one anionic surfactant.

Non-limiting examples of anionic surfactants are disclosed in McCutcheon's Detergents and Emulsifiers, North American Edition (1986), published by Allured Publishing Corporation; McCutcheon's Functional materials, North Americas Edition (1992), both of which are incorporated by reference into the subject application.

Examples of anionic surfactants include sarcosinates, sulfates, isethionates, taurates, phosphates, lactylates, glutamates and mixtures thereof. Among isethionates are preferred alkoxyl isethionates such as sodium cocoyl isethionate, sodium lauroyl isethionate and mixtures.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium, magnesium and triethanolamine. Another suitable class of anionic surfactants are the water-soluble salts of the organic, sulfuric acid reaction products of the general formula:

wherein $R_1$ is chosen from the group consisting of a straight or branched chain, saturated aliphatic hydrocarbon of radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and $\epsilon_\gamma$-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts or ammonium or triethanolamine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853.

Other useful anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further non-limiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Non-limiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are alkylamino carboxylates such as glutamates, especially those having carbon chains between $C_8$ and $C_{16}$. Non-limiting examples of glutamates include ammonium, sodium, potassium and alkanolamine (e.g., triethanolamine) salts of lauroyl glutamate, myristoyl glutamate, and cocoyl glutamate.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures therefor.

Especially preferred for use herein is ammonium lauryl sulfate, ammonium lauryl ether sulfate, sodium lauryl ether sulfate, sodium lauroyl sarcosinate, sodium cocoyl sarcosinate, sodium myristoyl sarcosinate, sodium lauroyl lactate, and triethanolamine lauroyl lactylates.

Nonionic Lathering Surfactants

Non-limiting examples of nonionic lathering surfactants for use in the compositions of the present invention are disclosed in McCutcheon's, Detergents and Emulsifiers, North American Edition (1986), published by allured Published Corporation; and McCutcheon's, Functional materials, North American Edition (1992); both of which are incorporated by reference herein in their entirety.

Nonionic lathering surfactants useful herein include those selected form the group consisting of alkyl glucosides, alkyl polyglucosides, polyhydroxy fatty acid amides, alkoxylated fatty acid esters, alcohol ethoxylates, lathering sucrose esters, amine oxides, and mixtures thereof.

Alkyl glucosides and alkylipolyglucosides are useful herein, and can be broadly defined as condensation articles of long chain alcohols, e.g., C8–30 alcohols, with sugars or starches or sugar or starch polymers i.e., glycosides or polyglycosides. These compounds can be represented by the formula $(S)_n$—O—R wherein S is a sugar moiety such as glucose, fructose, mannose, and galactose; is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably C7–$C_{19}$ alkyl or alkenyl, more preferably $C_9$–$C_{17}$ alkyl or alkenyl, most preferably $C_{11}$–$C_{15}$ alkyl or alkenyl; and Z is a polyhydroxy hydrocarbyl moiety having a linear hydrocarbyl chain with at least 3 hydroxyl directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. As especially preferred surfactant corresponding to the above structure is coconut alkyl N-methyl glucoside amide (i.e., wherein the $R^2CO$-moiety is derived form coconut oil fatty acids). Processes for making compositions containing polyhydroxy fatty acid amides are disclosed, for example, in GB Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798 to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxyl alkyl radical of from about 8 to about 18 carbon atoms, from 0 to about 10 ethylene oxide moieties, and from 0 to about 1 glyceryl moiety, and $R_2$ and R3 contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyidodecylamine oxide, oleyldi(2-hydroxyethyl) amine oxide, dimethyloctylamine oxide, dimethyldecylamine oxide, dimethyl-tetradecylamine oxide, 3,6,9-trioxaheptadecyidiethylamine oxide, di(2-hydroxyethylytetradecylamine oxide, 2-dodecoxyethyidimethylamine oxide, 3-dodecoxy-2-hydroxypropyldi(3-hydroxypropyl)amine oxide, diemethylhexadecyclamine oxide.

Non-limiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, *Detergents and Emulsifiers*, North American Edition (1986), published by Allured Publishing Corporation; and McCutcheon's, *Functional Materials*, North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonaine 16SP from Lonza Corp.), lauryl bis-(2-hydroxyethyl) carboxymethyl betaine, oleyl dimethyl gamma-carboxypropyl betaine, lauryl bis- (hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH$_2$)3 radical is attached to the nitrogen atom of the betaine),oleyl betaine (available as amphoteric Velvetex OLB-50 from Henkel), and cocamidopropyl betaine (available as Velvetex BK-35 and BA-35 from Henkel).

Example of sultaines and hydroxysultaines include materials such as cocamidopropyl hydroxysultaine (available as Mirataine CBS from Rhone-Poulenc).

Preferred for use herein are amphoteric surfactants having the following structure:

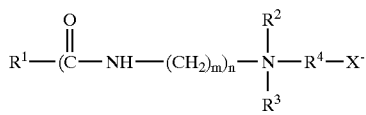

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected form the group consisting of $CO_2$, $SO_3$ and $SO_4$; $R^4$ is selected form the group consisting of saturated or unsaturated, straight or branched chain alkyl, unsubstituted or mono-substituted with hydroxy, having from 1 to about 5 carbon atoms. When X is $CO_2$, $R^4$ preferably has 1 to 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine);

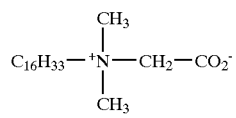

Cocamidopropylbetaine
wherein R has from about 9 to about 13 carbon atoms.

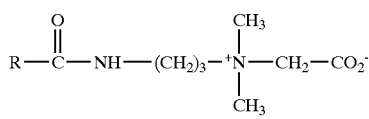

Cocamidopropyl hydroxy sultaine

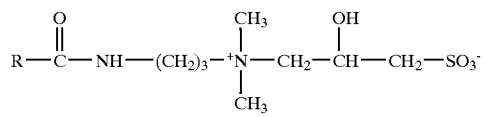

wherein R has from about 9 to about 13 carbon atoms.
Cationic Surfactants

Cationic surfactants are another useful class of surfactants that can be employed as auxiliary agents. They are particularly useful as additives to enhance skin feel, and provide skin conditioning benefits. One class of cationic surfactants is heterocyclic ammonium salts such as cetyl or stearyl pyridinium chloride, alkyl amidoethyl pyrrylinodium methyl sulfate, lapyrium chloride.

Tetra alkyl ammonium salts is another useful class of cationic surfactants. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides; behenyl dimethy ammonium chloride.

Other types of cationic surfactants that can be employed are the various ethoxylated quatemary amines and ester quats. Examples are PEG-5 stearyl ammonium lactate (e.g., Genamin KSL manufactured by Clarion), PEG-2 coco ammonium chloride, PEG-15 hydrogenated tallow ammonium chloride, PEG 15 stearyl ammonium chloride, dialmitoyl ethyl methyl ammonium chloride, dipalmitoyl hydroxyethyl methyl sulfate, strearyl amidopropyl dimethylamine lactate.

Still other useful cationic surfactants are quaternized hydrolysates of silk, wheat, and keratin proteins.
Polydextrose The compound which added to the formulation which induces formation of biphasic (multiphasic) liquid is polydextrose. Generally, the polydextrose has a formulation as follows:

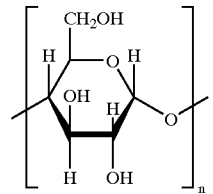

wherein n (defining number of linking glucose units) is preferably, but not necessary, from about 4 to about 22.

The preferred biphasic inducing polydextrose compounds of the invention noted above may also be defined by molecular weight in that they should have MW range of from 600 to about 3600, more preferably 700 to 3000, more preferably 700 to 1800, more preferably 900 to 1500, even more preferably 900 to 1200.

It should be understood that the critical point is that the structure is such as to induce formation of a multiphasic/biphasic formulation defined by those characteristics which in turn define the biphasic liquid (e.g., viscosity and stability in the biphasic state).

The amount of polydextrose used to induce biphasic state may vary depending on whether salt/electrolyte is used. Further, salt is preferably used (as well as stabilizer) if MW of polydextrose is sufficiently high.

Generally, whether or not salt is used (use of no or little salt also distinguishes this invention from other biphasic liquids of the art where relatively large amounts of salt, e.g., greater than 3% by wt., are in fact required to induce the biphasic liquid), there is needed at least 2.5% by wt., preferably at least 10% by wt. of polydextrose to induce biphasic separation. Generally, if less than,10% polydextrose is used, at least 2% salt will be needed.

There is generally a balance between the amount of surfactant used and the amount of polydextrose or sucrose. Generally lower surfactant requires more polydextrose or sucrose and, conversely, more surfactant requires less polydextrose or sucrose.

Generally, the upper limit of polydextrose used is about 75%. This is not an upper limit with regard to inducing biphasic liquid.

In addition, there is some interplay between molecular weight of polydextrose and use of salt. Thus, although not required, if MW of polydextrose is above 1800, preferably at least 0.1%, more preferably at least 0.5%, salt should be used. This is because the higher MW polydextrose tends to form a more opaque lower layer which salt helps stabilize.

In this embodiment, it is even further preferred to add stabilizers. Among the stabilizers which are preferred, but not necessarily used, include gums such as xanthan gum, guar gum or chemically modified guar gums. Other stabilizers include hydrophobically modified polyethers, hydrophobically modified acrylates and hydrophobically modified polyurethanes, all of which are described in the "optional" section below. If used, the stabilizers may comprise 0.01 to 3.0%, preferably 0.01 to 1.0% by wt. of the composition.

A third requirement of the invention is sucrose. Generally, sucrose will have structure as follows:

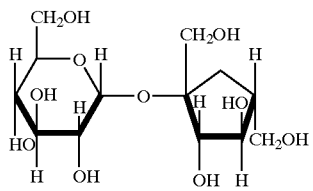

Generally, at least 2.5%, preferably at least 10% sucrose is used and levels can be as high as 5%, preferably no higher than 40%.

If electrolyte/salt is used, it typically will be used in amount of 0.5% to no higher than 4%, preferably no higher than about 3% by wt. of total composition. However, if less than about 10% polydextrose is used, generally at least about 2% salt is needed.

Preferably, the electrolyte is not a chelating electrolyte (these are generally poor in biodegradability).

Typically, the electrolyte should be a salt of a sulphate, bisulfate, carbonate, bicarbonate, phosphate, chloride, etc. Examples include sodium sulphate, potassium sulphate, ammonium sulphate, sodium chloride, and magnesium chloride. Magnesium sulphate and sodium chloride are particularly preferred.

Finally, the balance of composition is water and minors.
Optional
The following optional ingredients may be used in the multiphasic/biphasic compositions of the invention.

The composition may contain polyalkylene glycol. The polyalkylene glycol should be an alcohol, glycol or polyether of minimal molecular weight which is not irritating to the skin.

Examples of such include alcohols, particularly polyalkylene oxides having MW 200–6000, preferably 200 to 3000. The polyalkylene glycol can be comprised of ethylene oxide, propylene oxide, butylene oxide or their mixtures either as polymers or copolymers. Specific examples include polyethylene glycols such as PEG 400. As noted, use of such alcohols is not required.

The composition may further comprise thickeners. Generally, the thickener/viscosity modifier serves to thicken the upper and/or lower layer. As noted above, when MW of polydextrose is above 1800, use of stabilizer/thickeners (as well as salt) are particularly preferred.

Thickeners which may be used, generally, include hydrophobically modified polyethers. Examples of this class of thickeners which may be used include but are not limited to sugar esters such as PEG (160) sorbitan triisostearate (Rheodol TWS -399C ex Kao Chemicals) or PEG-120 Pentaerythrityl Tetrastearate ex Croda. Other examples include Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt); and Carbopol® polymers from Noveon.

Another class of suitable polymers are hydrophobically modified cellulose ethers including but not limited to hydroxyethyl cellulose, hydroxypropylcellulose and cellulose ethers with long pendant chains such as nonoxynyl hydroxyethylcellulose (Amerchol Polymer HM 1500).

Another class of suitable polymers are the hydrophobically modified acrylate copolymers such as Antil 208® (ex Goldschmidt) (acrylate/steareth-50 acrylate copolymer).

Another class of suitable polymers are the hydrophobically modified polyurethanes such as Acrysol series (e.g., Acrysol RM-2020) from Rhom and Haas.

Another class of suitable thickeners are xanthan gums, guar gums and chemically modified guar gums.

In addition to the ingredients noted above, the compositions of the invention may contain hydrotropes including but not limited to short chain monohydric or dihydric alcohols, xylene sulphonate and hexylene glycol whose purpose is to avoid the formation of liquid crystal phases resulting from the separation of the surfactant material into the upper phase hence increasing its apparent concentration.

The compositions may comprise benefit agents. Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, polyols (e.g., saccharides), enzyme and $\alpha$- or $\beta$-hydroxy acid either alone or entrapped in an oily benefit agent.

The benefit agent may be found in either the upper or the lower layer depending on its solubility and partition coefficient, for example, oil may partition into the upper layer while more water soluble agents (e.g., $^s_x$-hydroxyacids) may go into the lower.

The compositions may comprise perfumes, sequestering agents such as EDTA EHDP in amounts 0.01 to 1%, preferably 0.01 to 0.05%; coloring agents, opacifiers and pearlizers such as zinc stearate, magnesium stearate, TiO2, mica, EGMS (ethylene glycol monostrearate) or styrene/acrylate copolymers.

The compositions may further comprise antimicrobials such as 2-hydroxy 4,2'4' trichlorodiphenylether (DP300), 3,4,4'-trichlorocarbanilide, essential oils and preservatives such as dimethyl hydantoin (Glydant XL 1000), parabens, sorbic acid etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used including Quatrisoft LM-200 Polyquaternium-24, Merquat Plus 3330-Polyquaternium 39; and Jaguar® type conditioners.

Composition may also include clays such as Bentonite® claims as well as particulates such as abrasives, glitter, and shimmer.

The compositions of the invention, when unmixed, have a viscosity of the lower layer which is lower than the viscosity of the upper layer and a density of the lower layer which is greater than the density of the upper layer.

The compositions of the invention, in a separated state, are also stable in that no recrystallization (e.g., in the lower layer) occurs even when left sitting for more than 6 months at temperature of 0° C.

Compositions of the invention have an experiential element in that they are intended to be agitated by the consumer to mix and form a single visible phase before separating again after a time, anywhere from about a few seconds to not more than about 24 hours.

When mixed, the compositions have a viscosity in the range of 100 to 700 cps/mPas at 25° C. is measured using RV spindle #2 at 10 RPM.

Finally, the packages in which the compositions are contained are preferably translucent or transparent. By this is meant that the materials (e.g., plastics) have a light transmittance of greater than 50%, preferably greater than 75%, more preferably greater than 85% as measured at wavelength of 460 nm as determined by standard spectroscopy method. In practical terms the package should be sufficiently transparent to permit the separation of the two or more layers to be visible to the naked eye.

Except in the operating and comparative examples, or where otherwise explicitly indicated, all numbers in this description indicating amounts or ratios of materials or conditions or reaction, physical properties of materials and/ or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

Methodology

Measurement of Viscosity

Description

Brookfield Viscometer was used to measure the viscosities of liquid and semisolid personal wash products at various shear rates.

Equipment

The instrument was a Brookfield DV-II+Viscometer which includes the stand, RV spindles, 600 ml beakers for loading samples, and a waterbath which is maintained at 25° C.

Operational Procedure

The water bath, which is set to 25° C., and Brookfield viscometer were turned on.

All spindles were removed from the viscometer, and the unit was zeroed.

Measurements:

The appropriate spindle and rotation should be selected such that the readings fall within an operational range determined by Brookfield for that spindle and rotation.

(a) 500 ml of sample product is poured into a 600 ml beaker;
(b) the beaker is then placed into the waterbath until the product reaches 25° C.;
(c) the appropriate spindle is then submerged into the product at a 45 degree angle to the surface of the product;
  i) if RV Spindle #1 is used, the spindle can be submerged at a 90 degree angle to the product surface.
(d) the viscometer is then lowered down, and the spindle is carefully attached to the lower shaft of the viscometer;
(e) the viscometer is then set to the appropriate rotational speed and the motor is turned on;
(f) the motor remains on for one complete rotation of the spindle, at which time the viscosity is read on the display and recorded;
(g) the viscometer and spindle are raised out of the product, the spindle is removed, and then cleaned off of all product.

Materials & Methods

Materials

TABLE 1

Raw Materials

| | Trade Name | Structure |
|---|---|---|
| Na-Laureth Ether Sulfate | Steol CS-230 | — |
| Coco Amido Propyl Betaine | Tegobetaine F-50 | — |
| Almeo Blend | Almeo Blend | — |
| Sorbitol | Sorbitol | CH₂OH–HCOH–HOCH–HCOH–HCOH–CH₂OH |
| Sucrose | Sucrose | (sucrose structure) |

TABLE 1-continued

Raw Materials

| | Trade Name | Structure |
|---|---|---|
| Glucose | Glucose | 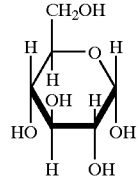 |
| Polydextrose (Av. MW = 3600)<br>Polydextrose (Av. MW = 1800)<br>Polydextrose (Av. MW = 1000)<br>Polydextrose (Av. MW = 720) | Maltrine M40<br>Maltrine M100<br>Maltrine M180<br>Maltrine M250 | 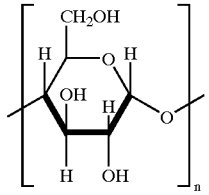 |
| Magnesium Sulfate | Mg*SO4 | — |

Formulation Preparation:

A simple solution of each ingredient was prepared at about 5 wt. % to about 60 wt. % without any saccharides. Then solutions were added to desired level. After adding all the solutions, samples were mixed and shaken to insure mixture was homogeneous. The samples were left undisturbed for 24 hours at room temperature and observations then made.

Viscosity & Product Appearance

Formulations were screened for viscosity using standard PW protocols as set forth in methodology section above. The formulations were observed for any discoloration and re-crystallisation of saccharides at room temperature.

EXAMPLES 1–4 AND COMPARATIVES

Table 2 below was made to show the effects of combination of polydextrose and sucrose.

TABLE 2

| Ingredients | Comp. A % wt/wt | Ex. 1 % wt/wt | Comp. B % wt/wt | Ex. 2 % wt/wt | Comp. C % wt/wt | Ex. 3 % wt/wt | Comp. D % wt/wt | Ex. 4 % wt/wt |
|---|---|---|---|---|---|---|---|---|
| Ammonium Lauryl Sulfate | 3.48 | 3.48 | 5.22 | 5.22 | 6.96 | 6.96 | 4.785 | 4.785 |
| Ammonium Lauryl Ether Sulfate | 3.48 | 3.48 | 5.22 | 5.22 | 6.96 | 6.96 | 4.785 | 4.785 |
| Cocomono-ethanolamide | 0.696 | 0.696 | 1.044 | 1.044 | 1.392 | 1.392 | 0.957 | 0.957 |
| Peg 5 Coco-monoethanolamide | 0.344 | 0.344 | 0.516 | 0.516 | 0.688 | 0.688 | 0.473 | 0.473 |
| Polydextrose M180 | 25 | 25 | 15 | 15 | 25 | 25 | 10 | 10 |
| Polydextrose M100 | — | — | — | — | — | — | — | — |
| MgSO4 | 1 | 1 | 3 | 3 | 0 | 0 | 2.5 | 2.5 |
| Minors (Fragrance, pH Adjusters, etc.) | — | — | — | — | — | — | 1 | 1 |
| Sucrose | — | 15 | — | 15 | — | 15 | 0 | 15 |
| Water | Q.S. to 100 | Q.S. to 100 | Q.S. to 100 | Q.S. to 100 | Q.S. to 100 | Q.S. to 100 | Q.S. to 100 | Q.S. to 100 |
| Biphasic | No | Yes, 40:60 | No | Yes, 60:40 | No | Yes, 90:10 | No | Yes, 80:20 |

As seen from Comparative A, B and D, use of salt alone in combination with polydextrose was not sufficient to induce biphasic formation. Only where sufficient sucrose was added, whether or not salt was present (see Example 3), did biphasic form.

EXAMPLES 5–9 AND COMPARATIVES

TABLE 3

Examples Demonstrating Sucrose

| Ingredients | Comparative % wt/wt | Example 5 % wt/wt | Example 6 % wt/wt | Example 7 % wt/wt | Example 8 % wt/wt | Example 9 % wt/wt |
|---|---|---|---|---|---|---|
| Ammonium Lauryl Sulfate | 2.175 | 2.175 | 17.4 | 17.4 | 5.22 | 5.22 |
| Ammonium Lauryl Ether Sulfate | 2.175 | 2.175 | 17.4 | 17.4 | 5.22 | 5.22 |
| Cocomonoethanolamide | 0.435 | 0.435 | 3.48 | 3.48 | 1.044 | 1.044 |
| Peg 5 Cocomonoethanolaide | 0.215 | 0.215 | 1.72 | 1.72 | 0.516 | 0.516 |
| Polydextrose M180 | 2.5 | 2.5 | 45 | 15 | — | — |
| Polydextrose M100 | — | — | — | — | 18 | 10 |
| MgSO4 | — | — | — | — | 1.5 | 3 |
| Xanthan Gum | — | — | — | — | 0.05 | 0.05 |
| Minors (Fragrance, pH Adjusters, etc) | — | — | — | — | ~2 | ~2 |
| Sucrose | — | 15 | — | 30 | 10 | 10 |
| Water | Q.S. to 100 | Q.S. to 100 | Q.S. to 100 | Q.S. to 100 | Q.S. to 100 | Q.S. to 100 |
| Biphasic | No | Yes, 95:5 | Yes, 95:5 | Yes, 95:5 | Yes, 70:30 | Yes, 70:30 |

Examples 5–7 shows varying levels of polydextrose (as low as 2.5%) and sucrose (as high as 30%) can be used.

In addition, Examples 8 and 9 show that different MW polydextrose can be used. As can be seen, at higher MW (polydextrose M 100), use of some salt, as well as stabilizer (e.g., xanthan gum) is preferred.

What is claimed is:

1. A liquid cleansing composition comprising:
   (a) about 5% to 75% by wt. of a surfactant selected from the group consisting of anionic surfactants, nonionic surfactants, amphoteric/zwitterionic surfactants, cationic surfactants and mixtures thereof;
   (b) at least about 2.5% of a polydextrose molecule or molecules;
   (c) about 2.5% to 50% sucrose; and
   (d) balance water and minors;
   wherein said composition comprises at least two visibly separated aqueous based layers when left sitting without shaking or stirring.

2. A composition according to claim 1, comprising 6% to 40% surfactant.

3. A composition according to claim 1, wherein the degree of polymerization of polydextrose is about 4 to about 22, corresponding to MW of about 600 to 3600.

4. A composition according to claim 3, wherein MW of polydextrose is 700 to 1800.

5. A composition according to claim 4, wherein MW is 900 to 1500.

6. A composition according to claim 5, wherein MW is 900 to 1200.

7. A liquid cleansing composition comprising:
   (a) about 5% to 75% by wt. of a surfactant selected from the group consisting of anionic surfactants, nonionic surfactants, amphoteric/zwitterionic surfactants, cationic surfactants and mixtures thereof;
   (b) at least about 2.5% of a polydextrose molecule or molecules;
   (c) about 0.5% to about 4% salt;
   (d) at least about 2.5% sucrose; and
   (e) balance water and minors;
   wherein said composition comprises at least two visibly separated aqueous based layers when left sitting without shaking or stirring.

8. A composition according to claim 7, comprising about 1% to about 3% salt.

9. A liquid cleansing composition according to claim 7, wherein molecular wt. of polydextrose is above 1800.

10. A liquid cleansing composition according to claim 9, additionally comprising 0.01 to 3.0% stabilizer.

* * * * *